US012415080B2

(12) United States Patent
Bagwell et al.

(10) Patent No.: US 12,415,080 B2
(45) Date of Patent: Sep. 16, 2025

(54) OSCILLATION-AIDED IMPLANT INSERTION SYSTEM AND DEVICE

(71) Applicant: Actuated Medical, Inc., Bellefonte, PA (US)

(72) Inventors: Roger B Bagwell, Bellefonte, PA (US); Alanoud S Alsubhi, State College, PA (US); Ryan S Clement, State College, PA (US); Jenna K Greaser, State College, PA (US); Eric M Steffan, Karthaus, PA (US); Natasha N Tirko, State College, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 692 days.

(21) Appl. No.: 17/704,698

(22) Filed: Mar. 25, 2022

(65) Prior Publication Data

US 2022/0379109 A1     Dec. 1, 2022

Related U.S. Application Data

(60) Provisional application No. 63/192,716, filed on May 25, 2021.

(51) Int. Cl.
*A61N 1/372*     (2006.01)
*A61B 17/34*     (2006.01)
(Continued)

(52) U.S. Cl.
CPC .......... *A61N 1/372* (2013.01); *A61B 17/3468* (2013.01); *B25B 11/007* (2013.01); *A61N 1/0551* (2013.01)

(58) Field of Classification Search
CPC .... A61N 1/372; A61N 1/0551; A61N 1/0529; A61N 1/0539; A61N 1/0558;
(Continued)

(56) References Cited

U.S. PATENT DOCUMENTS 4,047,532 A    9/1977  Phillips et al.
9,408,571 B2   8/2016  Gilgunn et al.
(Continued)

OTHER PUBLICATIONS

Matrix Array, https://www.neuronexus.com/products/electrode-arrays/3D-probes/large-animal-matrix-arrays; accessed Jun. 23, 2022 (3 pages).
(Continued)

*Primary Examiner* — Carl H Layno
*Assistant Examiner* — Mary Grace Schlueter
(74) *Attorney, Agent, or Firm* — Metz Lewis Brodman Must

(57) ABSTRACT

An implant insertion device includes a vibrational actuator generating axial vibrations, a coupler interconnected to the actuator and selectively retaining an implant with penetrating electrodes. The coupler has a distal end cavity at one end dimensioned to receive and retain at least a portion of the implant. Vibrations are transferred to the electrodes during insertion. A vacuum assembly connects to the coupler and
(Continued)

provides a negative pressure, or suction force, when a vacuum source is attached and activated. This suction force is sufficient to hold the implant to the distal end of the coupler. Deactivation of the vacuum source removes the suction force, causing the implant to detach from the coupler without perturbation of position. The insertion device may then be removed. A system to coordinate the operation of the actuator and movement of the device and/or tissue relative to one another for delivery of the implant is also provided.

22 Claims, 14 Drawing Sheets

(51) Int. Cl.
  *A61N 1/05* (2006.01)
  *B25B 11/00* (2006.01)
(58) Field of Classification Search
  CPC ............... A61N 1/375; A61N 1/37514; A61N 1/37518; A61B 17/3468; B25B 11/007
  USPC ........................................................ 607/115
  See application file for complete search history.

(56) References Cited

U.S. PATENT DOCUMENTS

| | | | |
|---|---|---|---|
| 2005/0273163 A1 | 12/2005 | Tran et al. | |
| 2006/0052796 A1* | 3/2006 | Perez ..................... | A61F 9/013 606/107 |
| 2007/0153405 A1 | 7/2007 | Kuiper et al. | |
| 2007/0156126 A1* | 7/2007 | Flaherty ............... | A61B 5/6885 606/32 |
| 2007/0173857 A1 | 7/2007 | Trieu et al. | |
| 2008/0221589 A1* | 9/2008 | Balling ................ | A61N 1/0551 606/129 |
| 2013/0204269 A1 | 8/2013 | Pynson | |
| 2017/0340891 A1 | 11/2017 | Boggs et al. | |
| 2018/0104478 A1* | 4/2018 | Hwang ................ | A61N 1/0551 |
| 2020/0368524 A1* | 11/2020 | Bagwell ............ | A61B 17/3468 |

OTHER PUBLICATIONS

Utah Array, https://blackrockneurotech.com/research/products/#electrodes, accessed Jun. 23, 2022 (8 pages).
Floating Microelectrode Arrays (FME), https://microprobes.com/products/multichannel-arrays/fma, accessed Jun. 23, 2022 (22 pages).
N-Form Insertion Tool, https://plexon.com/products/n-form-array-insertion-tool/, accessed Jun. 23, 2022 (9).
Excerpts from "Utah Array Surgical Manual (Research)" Mar. 2020, Blackrock Microsystems, LLC, pp. 1-8 and 23.
"N-Form® Array Insertion Tool: Directions for Use Neural Microelectrode Array Insertion Holder, Non-sterile", 2018 Plexon Inc., pp. P1-P5.
International Searching Authority; International Search Report and Written Opinion of the International Searching Authority; International Application No. PCT/US22/21990; Patent Cooperation Treaty; pp. 1-10; publisher United States International Searching Authority; Published Alexandria, Virginia, US; copyright and mailing date Jun. 21, 2022; (10 pages).
Atlas Neuro Accessories, https://www.atlasneuro.com/en/probes/accessories, accessed May 10, 2023 (7 pages).

* cited by examiner

OSCILLATION-AIDED IMPLANT INSERTION SYSTEM AND DEVICE

CROSS-REFERENCE TO RELATED APPLICATIONS

The present application claims priority to United States Provisional Application Ser. No. 63/192,716 filed on May 25, 2021, the contents of which are incorporated herein by reference in their entirety.

STATEMENT REGARDING FEDERALLY SPONSORED RESEARCH OR DEVELOPMENT

This invention was made with government support under NS105500 awarded by the National Institutes of Health/National Institute of Neurological Disorders and Stroke. The government has certain rights in the invention.

FIELD OF THE INVENTION

The present invention relates to the oscillation-aided insertion of implants which contain one or more electrodes for establishing a tissue interface through which to directly record and/or to stimulate activity in the target tissue. More specifically, the invention relates to a system to aid the insertion of implants, such as but not limited to neural implants, through the application of high frequency microvibration to the penetrating member(s) of the probe or electrode array to reduce the forces required to penetrate the tissue. The system also includes a vacuum coupling mechanism utilized to aid in implant retention during insertion and easy release of the implant once placed.

BACKGROUND

Implants, such as chronically implanted microelectrode arrays designed to interface with neural tissue, hold great potential for revolutionizing treatment of a range of medical conditions. Applications of neural implants include neural-based control of prosthetic limbs by amputees, brain-machine interfacing for paraplegics, selective ablation and/or inactivation of problematic neural pathways, or control or enhancement of organ function. Programs like SPARC, the BRAIN Initiative, and BrainGate are bringing new neuroprosthetic devices to patients, and researchers predict that neural implants will be more widely implemented in humans in the next 10 years. Non-penetrating neural implant electrode arrays such as EEG electrodes and nerve cuffs have seen increased clinical application in recent years, but such systems have limited spatial resolution, making them less ideal for future applications requiring more precise stimulation or recording. Penetrating neural electrode arrays offer significantly improved temporal and spatial resolution but suffer from multiple complications which restrict their clinical use. A major complication is the limited ability to precisely position the electrode array's penetrating members, or shanks, in the desired location, which is exacerbated by tissue compression and deformation, particularly when the electrode array consists of multiple closely spaced penetrating members, as in the "bed of nails" designs of the Utah (Blackrock) or microwire electrode arrays. The mechanical stress of implantation may also lead to penetrating member damage or bending and deflection that further exacerbates the tendency to miss the desired target or fail to penetrate the tissue altogether.

Additionally, the trauma of implantation, including the dimpling of local tissue and nerves, may decrease recording yield and can cause and/or accelerate glial scarring which isolates the implant from the target tissue. Chronically placed neural penetrating members that remain resident in tissue cause a reactive tissue response involving astrocytes and microglia that result in the formation of a cellular sheath or scar around the penetrating member. The response is highly complex with multiple chemical signaling pathways, cell types, and damage involved, but overall involves an initial acute phase of glial scarring in response to the initial injury followed by chronic inflammation. Previous studies comparing electrode insertion speeds have found that both electrophysiological and histological outcomes are more favorable with faster insertion so the faster insertion is often the approach typically used. Studies exploring the role of the electrode array density are largely lacking in the literature. However, given the fact that gliosis can often extend 500-600 µm beyond the implant-tissue interface, it is likely that there is compounding interaction among penetrating members that have overlapping regions of influence. In addition, more densely packed penetrating members will likely increase the implantation trauma and dimpling.

A subset of neural implants—penetrating intracortical microelectrode arrays—are composed of multiple penetrating members with typical cross-sectional diameters in the range of 25-100 µm and are typically implanted 0.25-2 mm into brain tissue, but sometimes as deep as several centimeters when targeting deep brain structures in some animal species. The recording sites are relatively small with high impedance (>100 kΩ), a requirement for recording unit activity from individual neurons. Variations in penetrating electrode technologies include insulated metallic microwires, micromachined high density 3-D electrode arrays such as the Utah electrode array that are similar in geometry to microwire electrode arrays, and planar thin-film microelectrode arrays like Michigan probes, also known as NeuroNexus, composed of silicon or polymer substrates with multiple electrode sites along the penetrating members. In addition to material and method of fabrication considerations, penetrating electrode designs may differ in: (a) geometry, including but not limited to tip shape, size and spacing of the penetrating members; (b) attachment state relative to the neural target, such as fixed or floating; and (c) insertion strategy, including by hand, manually with a micromanipulator, pneumatic impact, or mechanized insertion at fast or slow speeds. As the density of penetrating members of the electrode array increases, it is more likely to dimple or compress the neural tissue during implantation. One strategy employed for implantation of Utah electrode arrays in brain and nerve tissue is to use a pneumatic, single-shot, high speed impact inserter to essentially hammer the implant into neural tissue at high velocity to reduce dimpling. Since the inserter only makes momentary contact with the electrode array, this single shot approach does not allow for fine adjustment or correction if the initial placement is not ideal, or when fine anatomic details vary across subjects. Successful insertion is still often heavily reliant on surgical skill and technique.

Most types of neural microelectrode arrays, including microwires, 3-D silicon, and 2-D planar silicon devices, have published examples demonstrating the ability to record neural activity upwards of a year or more in many different subjects. However, the consistency in performance of penetrating neural microelectrode arrays is highly variable. For instance, a group at University of Michigan now has a team of individuals experienced in implanting their microelectrode arrays in subjects, and approximately 67% of the time the implants record unit activity for 3-6 months or more. However, the remaining 33% of the electrode arrays often fail at around 6 weeks, suggesting that if the microelectrode arrays can make it beyond this critical window, they could record neural activity indefinitely. According to an informal survey by Schwartz, any given recording electrode site on a penetrating member may only have a 40-60% chance of recording chronic neural activity and essentially all conductive penetrating members do eventually fail.

Therefore, a way to insert penetrating electrodes into neural tissue in a manner that preserves the integrity of the electrodes and minimizes damage and trauma to the surrounding neural tissue is still needed, for increased accuracy of placement and long-term use of the resulting embedded electrodes.

Peripheral neural targets like the dorsal root ganglia, nerves, spine, and even muscle tissue in the arms and legs present an even greater challenge for penetrating neural implant placement than that encountered for relatively soft tissue in the cortex of the brain. Compared to the brain, penetrating microelectrode array technology has been largely under-utilized in both basic and applied peripheral nervous system research. There are numerous reasons for this including greater difficulty in accessing and stabilizing the neural targets during surgery and challenges associated with either dissecting, or getting the shanks to penetrate, the neural membranes (epineurium or dura). There is increasing interest, however, in achieving direct interfacing with neural tissues outside the brain and with an approach that reduces tissue damage and improves implant location accuracy, allowing placement for instance in or near specific fascicles or neural circuits. As an example, the urinary system is a target for placement of penetrating neural implants where a great clinical need exists. Neurogenic bladder dysfunction, or the interruption in neural communication between the control circuit and bladder muscles, occurs in a staggering 70-84% of spinal cord injury patients. After spinal cord injury, lower urinary tract dysfunction generally presents as a reflexive bladder and sphincter paralysis. This is of particular concern in the military veteran population, where an estimated 32,000 spinal cord injury veterans suffer from micturition disorders. Inadequate post-injury management of lower urinary tract dysfunction can lead to complications from infection to total renal failure, which was previously the leading cause of death after spinal cord injury.

The ability to store and eliminate urine is regulated by a dynamic neural circuit integrating information from brain, spinal cord and peripheral autonomic ganglia. The lower urinary tract coordinates activity between smooth and striated muscles in the bladder and urethral outlet, to both store urine and void it. Numerous interventions attempt to treat neurogenic bladder dysfunction: timed voiding, manual expression, medications, catheterization (both intermittent and indwelling), and surgical procedures. The current clinical standard of care for neurogenic bladder dysfunction patients remains catheterization, however all forms of catheterization are associated with risk of infection, which causes these patients an average of 16 office and 0.5 emergency room visits per year and possible hospitalization. Alternative treatments to restore function of the neurogenic bladder system have been developed with varying degrees of success. In addition to catheterization, mechanical solutions such as artificial urethral sphincters, stents, and pumps have been tested, however all have similar risks of infection and limited functional lifespans. Pharmacology treatments like anticholinergic medications can also be used to relax the hyper-reflexive bladder but have systemic side effects like dry mouth and blurred vision.

Electrical control of the bladder through neuroprosthetics would avoid the inconvenience, recurring cost, and associated infection risk of catheterization, as well as the systemic problems from pharmacological drug therapies. The effectiveness of electrical stimulation devices is limited by a number of factors including the stimulation target, the type of stimulating electrode, surgical access to nerves, and device longevity. However, the effectiveness of existing electrical stimulation devices is restricted by limited surgical access to the nerves, difficulty in electrode placement, and poor stimulation specificity. Initial attempts at a nerve-based bladder control device relied on non-penetrating electrode technologies such as nerve cuffs that excite a large portion of the pudendal nerve, but this approach requires spatially segregated stimulation to avoid simultaneous activation of antagonistic muscle groups of the bladder. Penetrating multichannel electrodes allow more spatially specific activation of nerve fibers that could significantly improve outcomes. However, implantation of penetrating electrodes into nerves remains a great challenge. Piercing the epineurium requires the electrode to withstand forces which may buckle or break the electrode. In addition, nerves typically compress (dimple), stretch, and/or roll, which prohibits effective electrode insertion, increases risk of trauma, bleeding and inflammation to the nerve tissue, and may accentuate the chronic foreign body response (FBR) leading to cell death, peripheral nerve scaring, and device failure. For clinically viable chronic penetrating nerve interfaces, the insertion forces must be substantially reduced and the nerve must be better stabilized during electrode insertion process in a way that is both minimally invasive and temporary.

Multiple stimulation targets have been examined as potential sites for restoration of urinary function, with varying success. These include electrical stimulation of the bladder, transcutaneous electrical stimulation of various nerves, stimulation of sacral roots and nerves, stimulation of the spinal cord, and stimulation of peripheral nerves. The latter two approaches require highly invasive surgical procedures and have failure rates as high as 40%. For instance, stimulation of the pudendal nerve with a surface linear electrode, laparoscopically placed in soft tissue adjacent to the nerve has been performed. This procedure successfully controlled micturition in patients with overactive bladder but the low-resolution stimulation of the entire pudendal nerve bundle was insufficient for treatment of other types of bladder dysfunction. The pudendal nerve is a particularly good target for human bladder control, having consistent fascicular anatomy between individuals. An alternative extraneural electrode device, called BION, has shown some success, though technical failures and migration of the electrodes once embedded prohibited reliability. To improve stimulation specificity and more stable interface for longevity of the electrical stimulation effectiveness, an intraneural penetrating electrode solution is necessary. A promising approach with potential for future clinical use would involve peripheral nerve stimulation, but only with improved surgical approach and utilizing penetrating electrode arrays.

Intraneural, or penetrating microelectrodes are placed directly in the peripheral nerve and solve several problems presented by cuff and other extraneurally placed electrodes for interfacing with peripheral neural targets. Penetrating microelectrodes can be longitudinally implanted or transversely implanted, offering different surgical implantation strategies. Penetrating microelectrodes grant specificity of stimulation, as individual electrode surfaces and combinatorial activation of electrode pairs can target independent fascicles. Peripheral nerves also have considerable freedom of movement as compared to brain or spinal cord, so penetrating electrodes can also be more resistant to migration, as they are embedded in the nerve and more likely to move with the nerve as it may move in the body when surrounding tissues are stretched.

A critical aspect for insertion of penetrating neural implants, whether for the central or peripheral nervous system, is the ability to securely retain and reliably release a wide range of implant shapes and styles. The implants, which are very small, often sub-millimeter dimensions on each side, need be securely retained so they do not move out of alignment with the insertion axis as they experience forces during penetration process. At the same time, the devices are often very fragile and extremely expensive to manufacture, so the means of retaining them needs to be gentle and not apply excessive mechanical forces that may crush, bend, or otherwise break the implant. Furthermore, the implant also needs to be easily released when it is positioned in the desired location in the tissue, without having to twist, turn, or apply excessive torque to the implant that may apply forces to the surrounding tissue or inadvertently move the implant out of the desired position.

Others have used various methods to retain and release implants into neural tissue, including vacuum insertion (Matrix Array from NeuroNexus), pneumatic inserters (Utah Array from BlackRock), suction cups (Floating Microelectrode (FMA) from Microprobes), and hooks (N-form from Plexon/Modular Bionics). However, these methods do not account for use of vibrations to aid in the impact of implant electrodes on neural tissue and do not securely retain the electrode to withstand vibration. What is missing is an approach that securely retains the implant while also allowing for stable release of the implant without disturbing its final placement.

There is still much room for improvement in the field of electrode use for neurological stimulation, particularly in the areas of penetrating electrodes, floating arrays that are not anchored to bone, and in-dwelling or embedded implants that remain resident in the tissue for extended periods of time.

SUMMARY

An implant insertion system and device for the accurate and precise delivery of penetrating electrodes of an implant into tissue is disclosed. Such tissue may be, but is not limited to, neural tissue including any tissues of the nervous system, including without limitation the brain (including the cortical brain as well as deeper brain structures), spinal cord, dorsal root ganglion, peripheral nerves and peripheral nerve bundles. The system and device provide enhanced placement, accuracy, and functionality of penetrating nerve electrodes by selectively and securely retaining an implant while simultaneously vibrating the implant during insertion. This vibration is transferred to the electrodes, reducing the force needed to penetrate the tissue and increasing insertion success while also reducing strain and trauma to the neural tissue. Cessation of the vacuum provides selective release of the implant once it is embedded at the desired location. As a result of the combined vacuum and vibrations, the system and device of the present invention improves implant delivery and location accuracy, allowing placement in and near specific tissue areas, cortical targets, and/or nerve fascicles for highly specific electrode placement, neural stimulation, and recording of neural activity, without perturbing the location of the implant during the release and retraction of the delivery device.

The system and device of the present invention can be used for the insertion and placement of any type of implant with penetrating electrode, including stimulating and recording electrodes. The implant may include any number of penetrating electrodes, which can include a single electrode or array of multiple penetrating members. The implant may be made of many different types of biocompatible materials, including but not limited to microwire, silicon, carbon fiber, optical fiber, and/or polymers and various composites. The system and device can also be used to facilitate the insertion of thinner and more flexible implants and electrodes than current insertion options allow for. The current invention reduces the insertion force, implant buckling and breaking, and tissue dimpling to allow improved neural interface establishment. Longer electrodes and probes can be more successfully inserted to a target location due to reduced buckling and deflection.

The device of the present invention may be hand-held in some embodiments, mounted on a frame, such as but not limited to a stereotaxic frame in tabletop embodiments, and may be deployable through a trocar or laparoscope for clinical use and minimally invasive procedures in still further embodiments.

The implant insertion device of the present invention includes a vibrational actuator, which may be an ultrasonic actuator, configured to generate and deliver micro-vibrations to an implant. The vibrations are provided axially along the insertion axis of the device, which coincides with the longitudinal direction of the electrodes of the implant, to oscillate the electrodes during insertion into target neural tissue. A translational motor may also be included in the system to move the device linearly along the insertion axis, to advance the penetrating electrode(s) along a desired path at a controlled speed into the target neural tissue and to release and retract the supporting components of the system and device once the implant is embedded in the target neural tissue. The system also includes a control unit with a processor and vibrational and translational drivers. The vibrational actuator and translational motor are each in electrical communication with the control unit and receive operative instructions from the respective drivers to activate and operate.

The device also includes a coupler configured to selectively retain and reliably release the implant having at least one electrode. The coupler is interconnected with the vibrational actuator and transmits the axially-directed vibrations to the implant and electrode(s) during insertion. The distal end of the coupler is dimensioned to receive and retain at least a portion of the implant and, in certain embodiments, may have a cavity formed therein which is correspondingly shaped to receive and retain at least a portion of a base of the implant therein. The cavity may further include at least one notch or other feature to accommodate tabs or other corresponding features of the implant to enhance retention of the implant within the distal end cavity, prevent from rotation within the cavity, and transmit vibrations to the implant. In some embodiments, the distal end cavity may also receive a seal to contour to the implant, provide increased stability and reduce air leakage around the implant. A lumen extends through the coupler, terminating at the distal end cavity and transferring negative pressure from a vacuum source to the implant and retaining the implant in the distal end cavity.

When present, the seal may include an aperture corresponding to the coupler lumen and allowing the negative pressure through to the implant.

The device also includes a vacuum assembly comprised of a vacuum connection body and vacuum tubing. The vacuum connection body connects to the vibrational actuator at one end and to the coupler at the opposite end, providing a path for transmission of vibrations from the actuator to the coupler. An arm extends from the vacuum connection body and connects to the vacuum tubing, which in turn connects to a vacuum source. Each of the vacuum tubing, arm, and vacuum connection body includes a lumen, forming a path therethrough. The lumen of the vacuum connection body aligns with the lumen of the coupler, defining a vacuum path through the coupler and vacuum assembly. When a vacuum source is connected and powered on, it creates suction force which is transmitted through the vacuum path to the implant, providing sufficient negative pressure to retain the implant in the coupler.

To insert an implant into target tissue using the present system, the device may be aligned with and spaced apart from tissue before the implant is attached. A vacuum source is turned on to attach the implant through negative pressure exerted thereon. The implant is then inserted into tissue by turning on the vibrational actuator and advancing the device, now with attached implant, toward the target tissue, causing the electrodes to pierce the tissue and penetrate the tissue until the desired location is reached. Once desired positioning is confirmed, such as through a visualization aid, the vibrational actuator is turned off, the vacuum source is turned off releasing the implant from the device, and the device without the implant is removed from the tissue area.

The implant insertion system and device, together with their particular features and advantages, will become more apparent from the following detailed description and with reference to the appended drawings.

DETAILED DESCRIPTION

Figure 1:
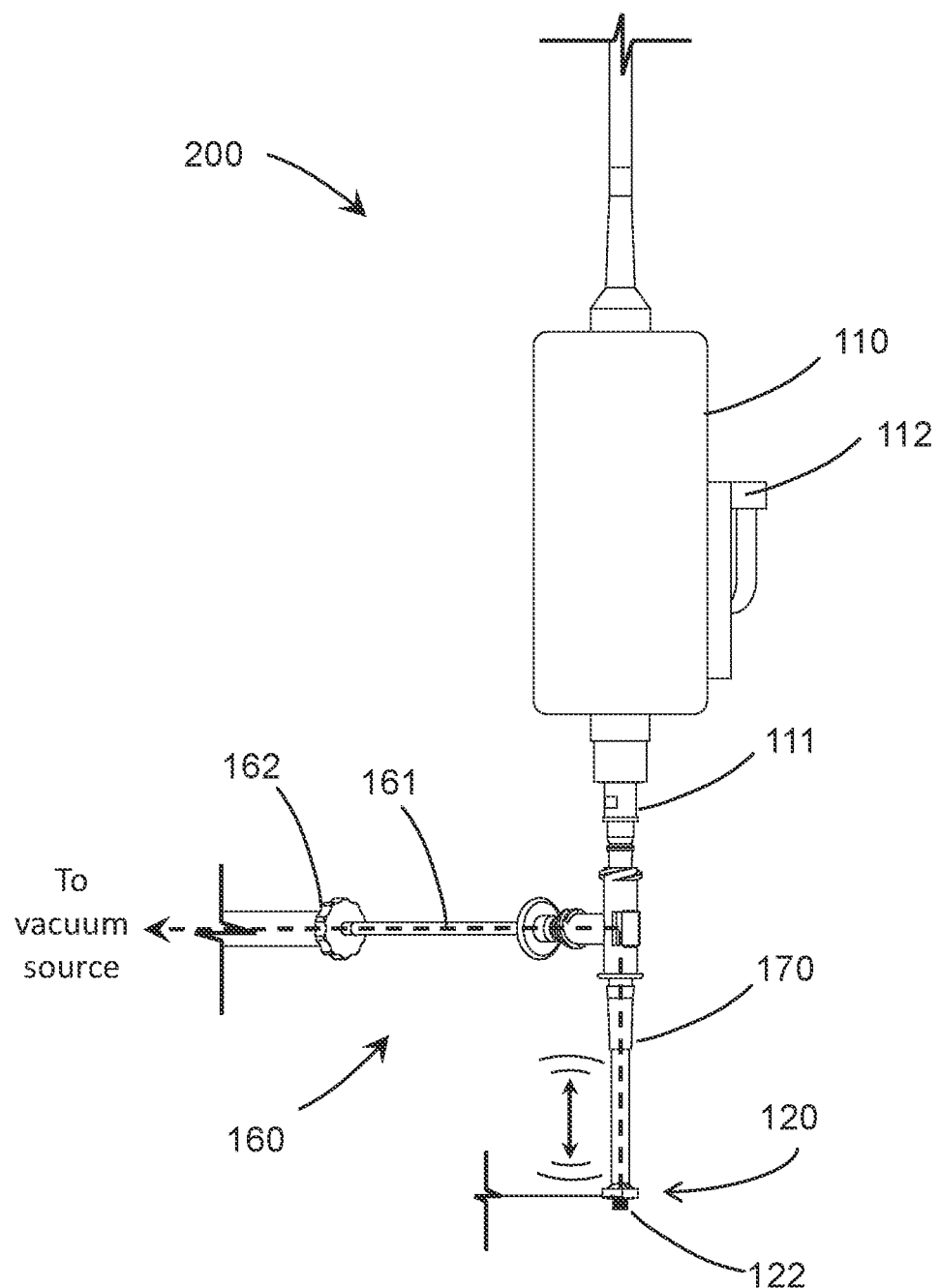
FIG. 1 is a perspective view of an illustrative embodiment of the implant insertion device of the present invention with an implant attached.

As shown in the accompanying drawings, the present invention is directed to an implant insertion system 100 and device 200 for the precise delivery of an implant 120 having electrode(s) 122 into tissue 5. The device 200 and system 100 can be used to insert one or more electrode penetrating members 122, either singly or in an array as part of an implant 120, into a desired target tissue 5. The device 200 and system 100 use vacuum force to retain the implant 120 during insertion. Vibrations are also generated and propagated to the implant 120 during insertion to reduce the forces necessary to penetrate the tissue and to reduce dimpling of the tissue that is being penetrated, resulting in a more precise placement. Further, the vibrations may reduce the FBR byproducts of the body's defense system response to the electrode(s) 122. Once inserted to the desired location within the tissue 5, the vacuum is deactivated to release the hold on the implant 120 and permit the device 200 to be retracted without perturbing the position of the implant 120 from its location within the tissue 5. The objective of the system 100 is to improve insertion ease and precision while reducing strain and trauma to recipient tissue for increased implant success.

Though described in terms of neural tissue herein for the sake of simplicity, the tissue 5 may be any type of tissue, such as, but not limited to, neural tissue, connective tissue, epithelial tissue, and muscle tissue. In at least one embodiment, the tissue 5 is neural tissue, including but not limited to brain tissue (including cortical and/or deep brain structures), the spinal cord, and peripheral nerves. Penetrating electrode arrays are preferable to superficially applied arrays for neural stimulation because they allow for specificity of stimulation, as individual electrodes can target independent fascicles and/or neural circuits when inserted and/or embedded. Activation of opposing functions may be avoided if appropriate populations of nerve fibers within individual fascicles or specific neurons of a circuit or center can be selectively targeted.

As shown throughout the Figures, the present implant insertion system 100 and device 200 may be used to insert an implant 120 into target tissue, such as a neural implant into neural tissue. The implant 120 is comprised of at least one electrode 122 extending from a base 124. Electrode(s) 122 may also be referred to alternatively as the "shank(s)" or "penetrating member(s)" of an implant 120. An implant 120 having more than one electrode 122 may also be referred to herein as an "array". The base 124 may hold all the electrodes 122 together in the implant 120.

Any neural implant 120 may be used, including but not limited to multi-channel, single-shank devices like Qualia Labs Softening Brain Probes; arrays having multiple electrodes 122 including but not limited to NeuroNexus, BlackRock, and Modular Bionics N-Form probes; and microwire arrays such as but not limited to those manufactured by Tucker-Davis Technologies or MicroProbes for Life Sciences. In some embodiments, the implant 120 may include an array of multiple electrodes 122 of any number, distribution, and arrangement of electrode shanks. One example is a 2×4 microarray, though other configurations are contemplated. For instance, the implant 120 may have two, three, four, six, eight, twelve, or more electrodes 122. In other embodiments, the implant 120 may be a single electrode 122, which may be mounted to and extend from a post as a base 124. The implant electrode(s) 122 may be made of any biocompatible material, such as but not limited to tungsten, silicon, and polymers. They can have any tip angle or shape, such as blunt, rounded, or angled. In some embodiments, the implant 120 may be composed of material to transmit light into or from the neural tissue, such as penetrating members containing optical fibers, or of a material to transmit fluid flow into or from the neural tissue, such as penetrating members containing fluid channels or dialysis membranes.

A major contribution to the failure of electrodes over time is believed to be the mismatch in stiffness between the target tissue and the neural implant. For example, a stiff or rigid electrode 122 can injure the surrounding softer tissue as a result of mechanical motion, which can in turn induce a damaging tissue response. Flexible and/or ultra-fine implants, such as 7-8 µm diameter carbon fibers, are therefore desirable but are much more difficult to insert through tough tissues, such as peripheral nerve targets. The challenge of inserting an electrode(s) 122, particularly a flexible one, is to ensure the force required to penetrate brain tissue or the tough epineurium layer in the peripheral nervous system remains below the buckling force of the implanted electrode(s) 122 of the neural implant 120. This challenge may become more exaggerated as implants 120 and their corresponding electrodes(s) 122 become finer, use different electrode shanks or electrode(s) 122, or more dense arrays of electrode(s) 122.

The implant 120 may be a fixed array that is affixed to the skull, bone, or other rigid material surrounding the target neural tissue, a tethered array on the end of a flexible cable 125 which is anchored elsewhere, or a completely floating array that is embedded in the target neural tissue 5 but are not affixed to any other material and can "float" within the tissue. In at least one embodiment, as shown throughout the Figures, the implant 120 is tethered, having a highly flexible cable 125 of wires extending from the base 124 to a controller that provides electrical communication between the electrodes 122 of the implant 120 and the controller which may send and receive information to and from the electrodes 122, such as but not limited to electrical signals. The cable 125 may include a single channel of electrical communication or multiple channels for the same or different types of communication. For example, the cable 125 may include multiple channels each dedicated and connected to a single electrode 122 from the implant 120. In other embodiments, the cable 125 may include multiple channels, such as at least one providing electrical communication with electrodes 122 and at least one other channel providing light energy, such as in the case of use of a fiber optic to deliver and/or collect light and light-based data. In still other embodiments, the various channels of the cable 125 may be configured and dimensioned to enable the transmission of fluid flow into or from the neural tissue, such as in the case of a probe or cannula.

Implant Insertion Device

FIG. 1 shows an illustrative embodiment of the implant insertion device 200 of the present invention. It includes a vibrational actuator 110 configured to generate vibrations or oscillations when activated. As used herein, the terms "vibration" and "oscillation" may be used interchangeably. The vibrational actuator 110 may be any motor capable of generating vibrations, preferably axial vibrations. For instance, in at least one embodiment the vibrational actuator 110 may be an ultrasonic actuator capable of generating vibrations in the ultrasonic range 0.1-20 µm. It may be operated at a resonant frequency in the range of 20-100 kHz and may preferably be operated at a resonant frequency in the range of 20-40 kHz. In at least one embodiment, the resonant frequency may be 23 kHz. In other embodiments, the vibrational actuator 110 may be a piezoelectric stack actuator with 23 kHz resonant frequency. In still other embodiments, the vibrational actuator 110 may be a voice-coil motor capable of generating vibrations at a lower frequency, such as in the range of about 100-200 Hz, and higher displacements (also referred to as amplitudes) such as up to hundreds of microns. In other embodiments, such as may be used in laparoscopic and other applications, the vibrational actuator 110 may be capable of generating vibrations with amplitudes in the range of 0.05 to 0.5 mm and at frequencies in the range of about 80-200 Hz. Regardless of how generated and the precise frequency, vibration displacement output may be controlled by increasing and decreasing the driving power provided to the vibrational actuator 110. The vibrations generated by the vibrational actuator 110 are preferably axial vibrations, created and propagating linearly along the longitudinal axis of the vibrational actuator 110. The vibrations reduce the force needed to penetrate tissue 5, for both "stiff" penetrating members 122 such as microwire or silicon material, as well as "flexible" penetrating members 122 such as comprised of carbon fibers, polyimide or parylene substrates.

The vibrational actuator 110 may also comprise an actuator connector 111 where the remainder of the device 200 selectively attaches. In some embodiments, the vibrational actuator 110 and actuator connector 111 may be a single composite structure. In other embodiments, the actuator connector 111 may be selectively affixed to the vibrational actuator 110 or housing thereof, providing a secure connection and permitting transmission of vibrations or oscillations produced by the vibrational actuator 110 to the remainder of the device 200.

The device 200 further includes a coupler 170 interconnected to the vibrational actuator 110, such as through the actuator connector 111. The coupler 170 provides a secure attachment of the implant 120 for insertion and faithful transmission of the vibrations from the vibrational actuator 110, yet quick release when desired without perturbing or disrupting the insertion site. Specifically, and with reference to FIG. 2, the coupler 170 has a proximal end 176 and an opposite distal end 172. The coupler 170 is a sufficiently rigid component that receives the vibrations from the vibrational actuator 110 at its proximal end 176 when such vibrations are generated and transmits those vibrations to the implant 120 at its distal end 172. The coupler 170 may be made of various materials suitable for transmitting vibrations therethrough, such as but not limited to aluminum, steel, and plastics such as but not limited to polycarbonate, photocured polymers, fused deposition modeling (FDM), or extruded plastics. The coupler can be formed by methods such as but not limited to 3-D printing and injection molding.

The distal end 172 of the coupler 170 includes a distal end cavity 173 formed therein, as shown in FIGS. 2, 4, 7B, 8B and 9B. The distal end cavity 173 is dimensioned to receive and selectively retain at least a portion of an implant 120 therein, such as the base 124 of an implant 120, as shown in FIGS. 3-9B. The implant 120 may be any type having at least one electrode 122 mounted to and extending away from a base 124, as described above. The distal end cavity 173 is configured to receive at least a portion of the base 124 of the implant 120. For instance, the distal end cavity 173 comprises a recess that is at least as large as the base 124 of the implant 120. In at least one embodiment as shown in FIGS. 3-9B, the distal end cavity 173 is correspondingly dimensioned to the size and shape of at least a portion of the base 124, which may include the entire base 124 of the implant 120. This cavity 173 is therefore configured to receive the implant 120, such as the correspondingly dimensioned base 124 therein, when loading the implant 120 into the insertion device 200. It is contemplated that the distal end cavity 173 may be shaped to accommodate implants 120 of various geometries. Implants 120 may be of any geometry at the base 124, such as but not limited to square, rectangular, circular, ovular, or any polygonal shape; the cavity 173 may be of any accommodating shape to receive the base 124 therein.

Figure 8A:
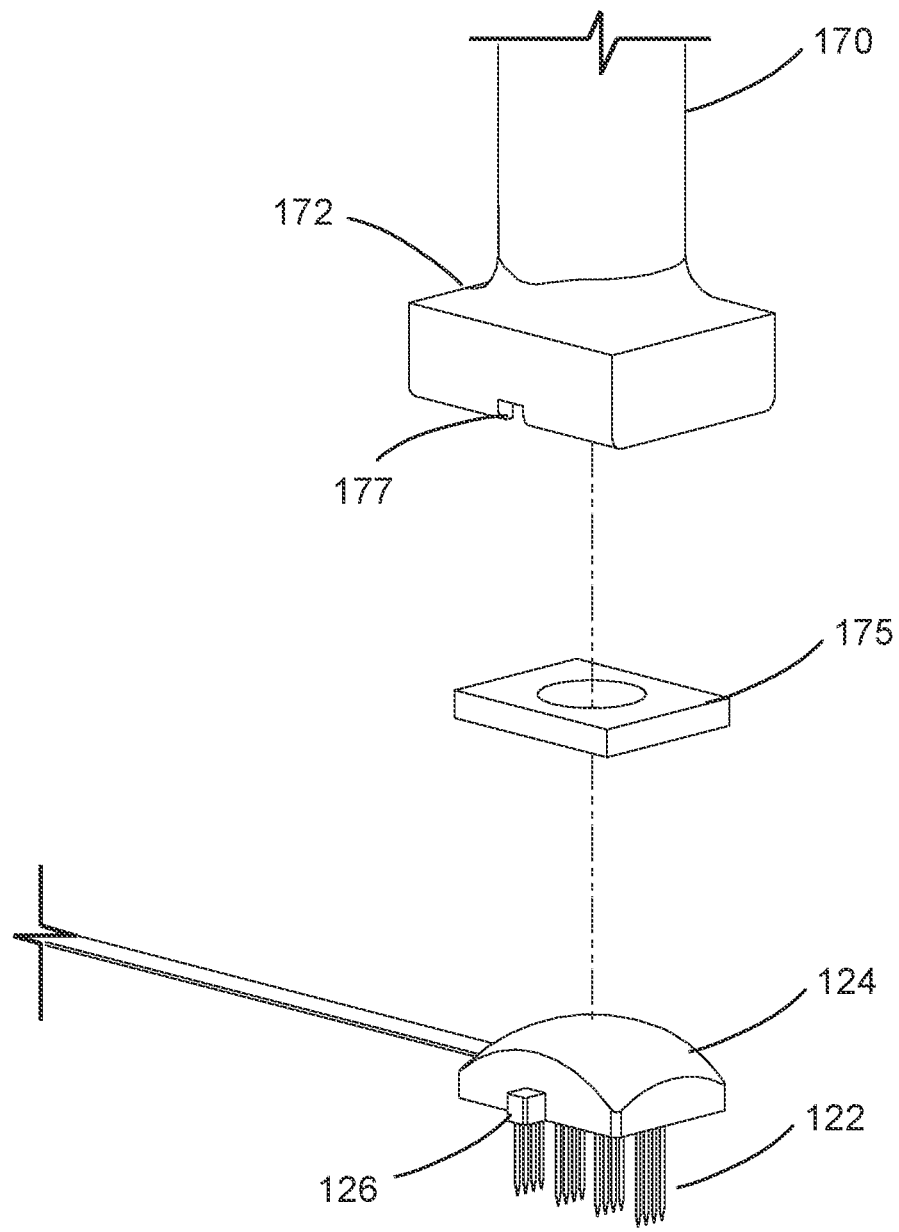
FIG. 8A is an exploded top perspective of a third embodiment of the coupler assembly and implant of the present invention, showing a non-planar implant base.
Figure 8B:
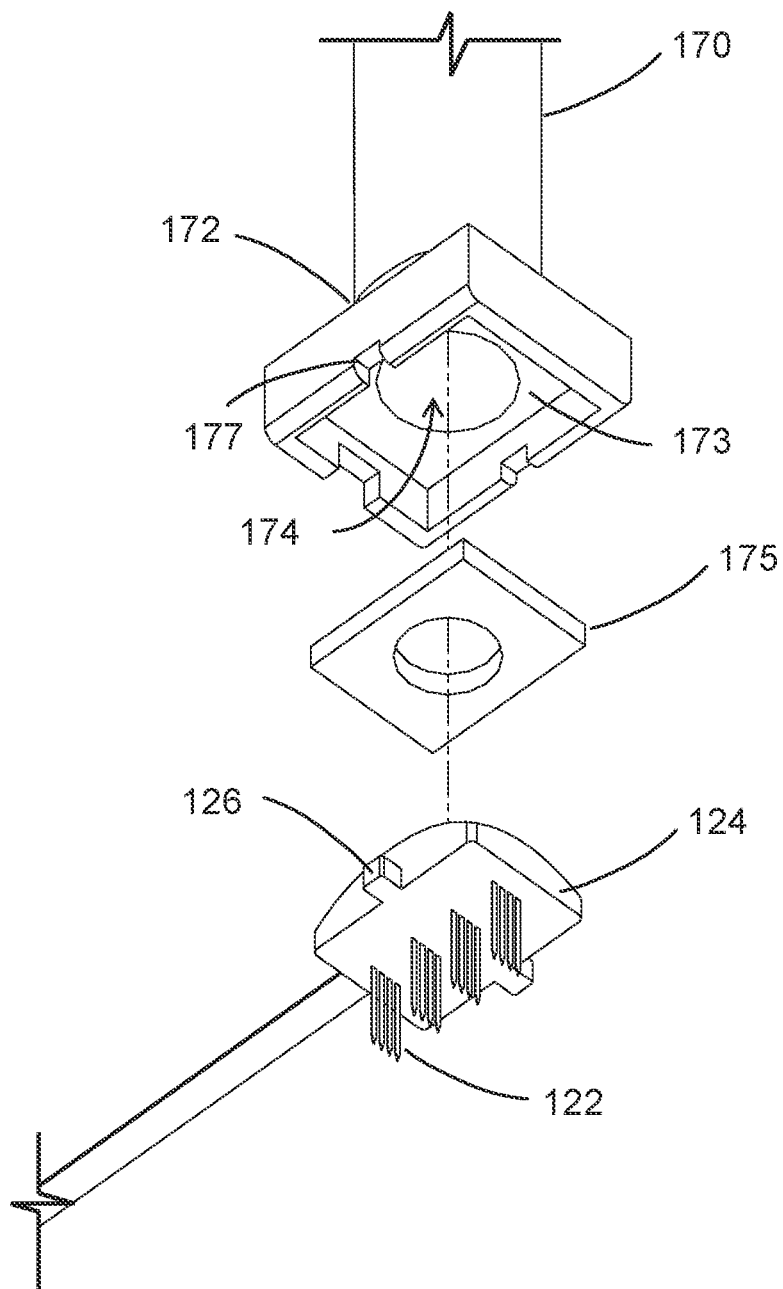
FIG. 8B is an exploded bottom perspective the coupler assembly and implant of FIG. 8A.
Figure 9A:
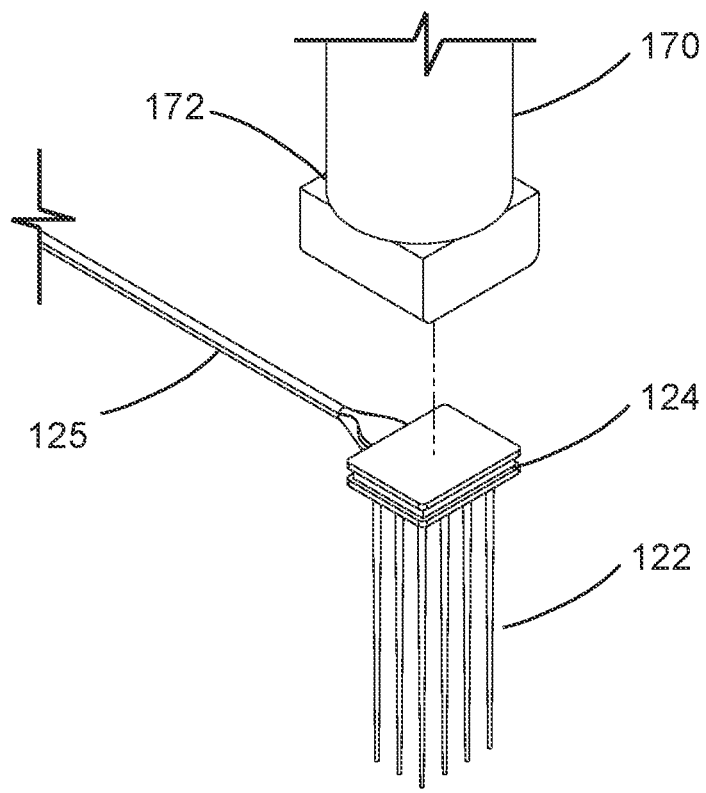
FIG. 9A is an exploded top perspective of a fourth embodiment of the coupler assembly and implant of the present invention, where tabs are not needed.
Figure 9B:
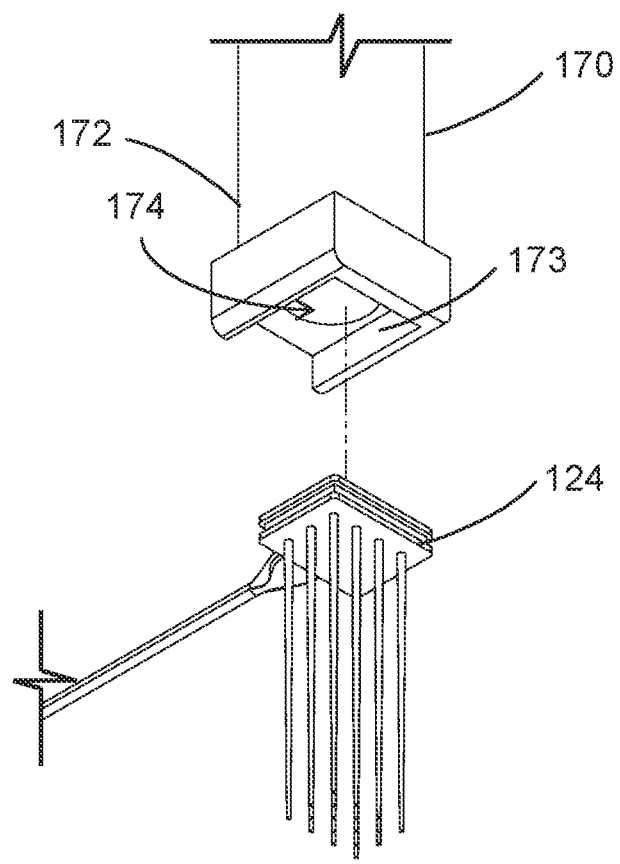
FIG. 9B is an exploded bottom perspective the coupler assembly and implant of FIG. 9A.

For instance, in the embodiments shown in FIGS. 3-7B, the implant 120 is rectangular with a substantially planar base 124. In the embodiment of FIGS. 8A-8B, the base 124 of the implant 120 may have a rounded geometry at the portion opposite the electrode(s) 122 which is received in the cavity 173 of the coupler 170. In embodiments as shown in FIGS. 3-8B, the implant 120 includes a tab 126 extending from at least one side of the base 124. The cavity 173 may have corresponding features to accommodate the tabs 126, such as a notch 177 shown in FIGS. 4, and 7A-8B. Each notch 177 receives a corresponding tab 126 when the implant 120 is loaded into the coupler 170 and provides both alignment and prevention of rotation of the implant 120 within the distal end 172 of the coupler 170. The tab(s) 126 therefore contact the distal end 172 of the coupler 170 when the implant 120 is retained therein. In at least one embodiment, the tab(s) 126 receive the vibrations from the coupler 170, transferring the vibrations to the remainder of the base 124 and on to the electrode(s) 122 which extend therefrom. In some embodiments, the tabs 126 may be the only portion of the base 124 contacting the coupler 170. In other embodiments, the distal end cavity 173 may include a grooved, angled or curved pocket or have other configuration suitable to provide further stability and/or transfer of vibrational energy to the implant 120 during insertion. In still further embodiments, such as shown in FIGS. 9A-9B, the base 124 may not have tabs 126 extending therefrom.

Regardless of geometry, and as shown in the respective corresponding Figures, the distal end cavity 173 of the coupler 170 is configured to receive the implant 120 therein. Preferably, the shape and dimensions of the cavity 173 are sufficient to limit or prevent rotational movement of the implant 120 during insertion or placement into the target tissue 5. For instance, the cavity 173 may be surrounded by walls extending around the implant 120. Such walls may limit motion of the implant 120 during placement and, in at least one embodiment, aid in transferring vibrational energy to the implant 120 through implant tabs 126. In at least one embodiment, the distal end cavity 173 does not contact the electrode(s) 122 extending from the base 124 even when the implant 120 is fully seated within the cavity 173.

The coupler 170 also includes a coupler lumen 174 extending through the coupler 170 from the proximal end 176 to the distal end 172. The coupler lumen 174 is open to and in fluid flow communication with the interior of the distal end cavity 173, as shown in FIGS. 4, 7B, 8B and 9B, permitting air to be drawn into the opening of the coupler lumen 174 when a vacuum source (not shown) is activated. The coupler lumen 174 may be any diameter less than the outer diameter of the coupler 170, but in at least one embodiment has a sufficient diameter to allow air to be drawn therethrough, such as by the negative pressure or suction of a vacuum.

In some embodiments such as in FIGS. 3-4 and 8A-8B, a seal 175 may be positioned within the distal end cavity 173 between the implant base 124 and coupler 170. The seal 175 provides improved retention of the implant 120 within the cavity 173 by the vacuum source and minimizes air leakage between the implant 120 and the coupler 170. The seal 175 may contain an aperture which is similarly shaped and dimensioned as the coupler lumen 174 and aligns with the coupler lumen 174 when assembled in the device 200, allowing the negative pressure from a vacuum source to be transferred from the coupler lumen 174 to the implant base 124 for retention of the implant 120 in the distal end cavity 173. The seal 175 may be made of a resilient material that allows for compression so the seal 175 may conform to the geometry of the implant 120. Some examples include but are not limited to silicone, rubber and soft plastics or polymeric material. The seal 175 may provide structural stability during insertion while also permitting transmission of vibrational energy from the actuator 110 to the electrode(s) 122. In some embodiments, the seal 175 may function to provide an improved fit between the wall(s) of the distal end cavity 173 and the surfaces of the base 124 facing the cavity 173 when they are irregularly shaped or do not conform or correspond to the interior of the distal end cavity 173. These irregularly shaped or non-conforming surfaces may be caused by any feature of the implant such as, but not limited to, base 124 design and byproducts of manufacturing processes, and may include rounded rear surfaces of the base 124, such as depicted in FIGS. 8A and 8B.

Figure 2:
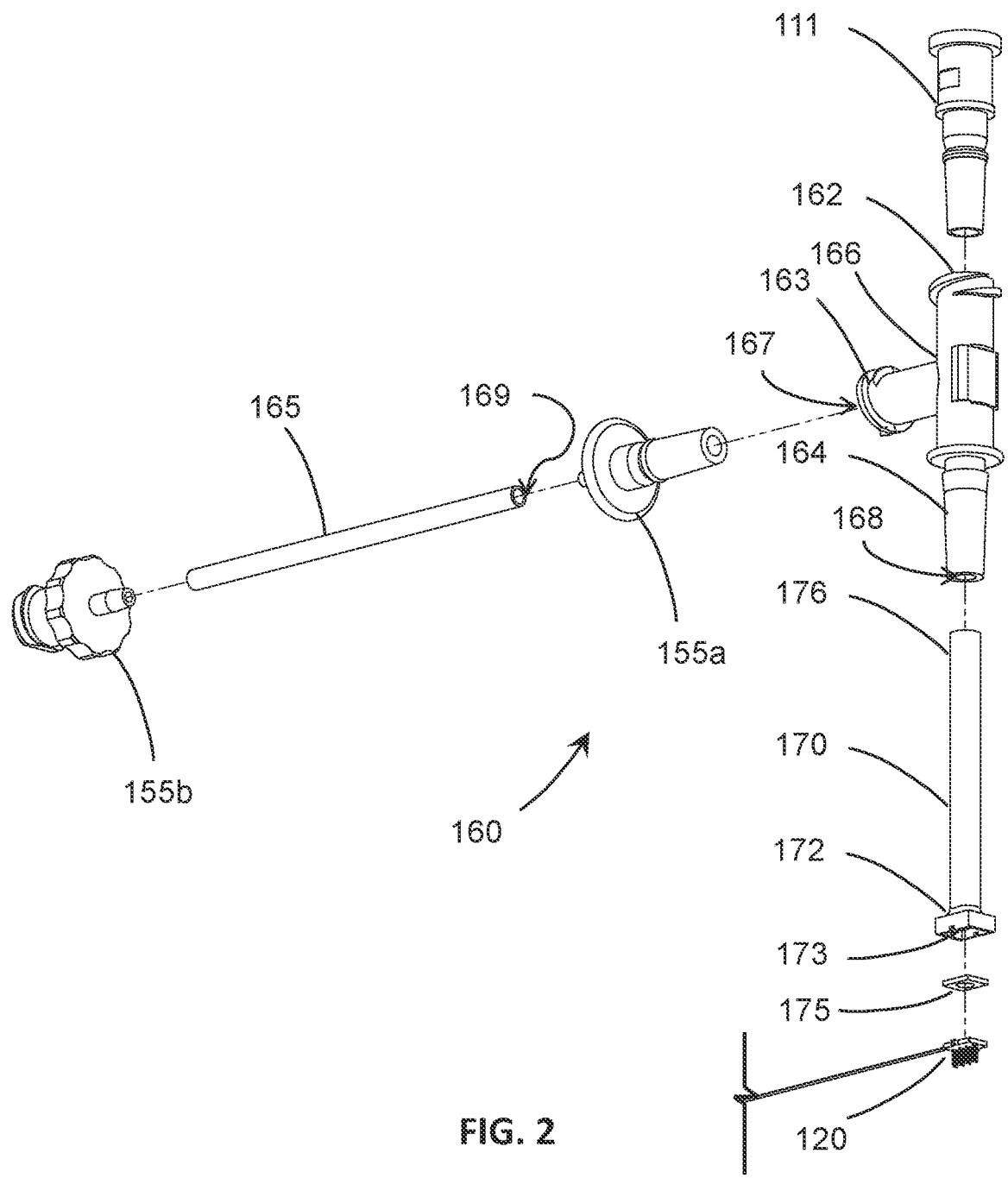
FIG. 2 is an exploded view of the vacuum assembly, coupler, and implant of FIG. 1.
Figure 3:
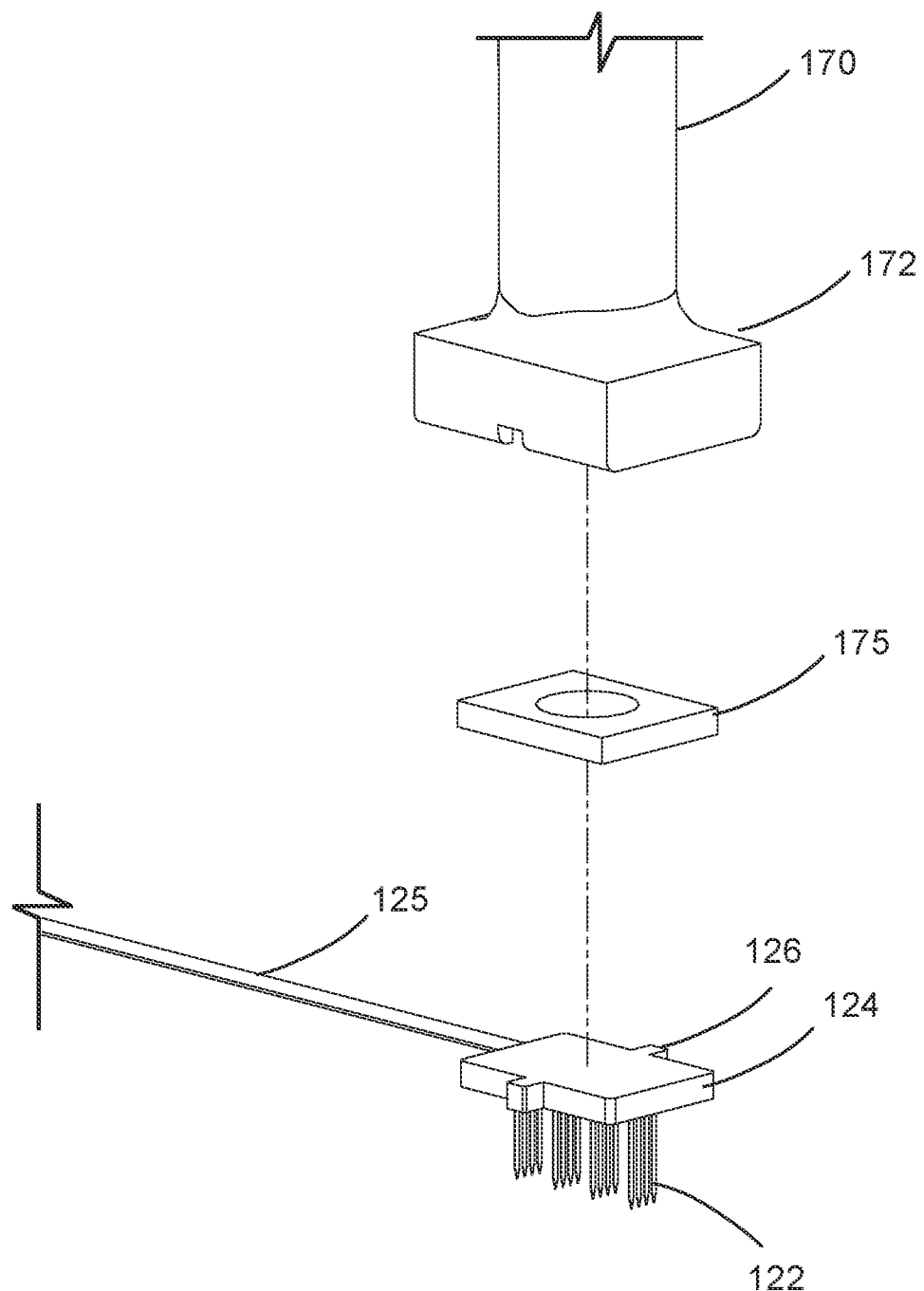
FIG. 3 is an exploded top perspective view of a first embodiment of the coupler and implant.

The implant insertion device 200 also includes a vacuum assembly 160, as depicted in FIGS. 1 and 2, which is responsible for providing the negative pressure (also referred to herein as suction or vacuum force) to the system 100 for the selective retention and release of the implant 120 at the coupler 170. In some embodiments, the vacuum assembly 160 may be a single component made from polymers, plastics or metals. Alternatively, the vacuum assembly 160 may consist of various components each made from polymers, plastics or metals. In addition, the vacuum assembly 160 may be located at any point in the device 200 between the vibrational actuator 110 and the implant 120. Preferably, the vacuum assembly 160 is positioned between the vibrational actuator 110 and the coupler 170, as shown in FIGS. 1 and 2.

The vacuum assembly 160 includes a vacuum connection body 166 having a first end 164 connected to the coupler 170, a second end 162 connected to the vibrational actuator 110, and an arm 163 extending from the vacuum connection body 166 between the first and second ends 164, 162. Accordingly, the vacuum connection body 166 is positioned between the vibrational actuator 110 and coupler 170 and may therefore also be of sufficiently rigid material to transmit vibrations from the actuator 110 to the coupler 170. The arm 163 may extend from the body 166 at any angle, but in at least one embodiment extends at a 90° angle relative to the length of the body 166 which is defined between the first and second ends 164, 162. Accordingly, the arm 163 may extend substantially transversely or perpendicular to the vacuum connection body 166.

The vacuum connection body 166 also includes a body lumen 168 extending through at least a portion of the vacuum connection body 166. It is sized and dimensioned to permit the flow of air therethrough for vacuum suction. The body lumen 168 terminates at the first end 164 of the vacuum connection body 166 and aligns with the coupler lumen 174 of the coupler 170 in fluid flow communication therewith. In some embodiments, the body lumen 168 may extend from the first end 164 to the second end 162 of the vacuum connection body 166, though in at least one embodiment the body lumen 168 may terminate prior to the second end 162 and therefore may not continue to the vibrational actuator 110. This may be as a result of the form and/or dimensions of the body lumen 168, or it may be from the inclusion of a gasket or blocking material such as but not limited to silicone or rubber in the vacuum connection body 166 that blocks the body lumen 168 above the arm 163.

The arm 163 of the vacuum connection body 166 also includes an arm lumen 167 that extends through the arm. The arm lumen 167 is in fluid flow communication with the body lumen 168 and is sized and dimensioned to permit air flow therethrough. The arm lumen 167 extends the full length of the arm 163, from the body lumen 168 at one end and the terminal end of the arm 163 on the other.

The vacuum assembly 160 also includes vacuum tubing 165 connected to the terminal end of the arm 163 at one end and to a vacuum source (not shown) at the opposite end. The vacuum tubing 165 may be compliant material, such as silicone or rubber, or it may be a more rigid material. Connectors 155a, 155b may be used at each end to connect the vacuum tubing 165 to the arm 163 of the vacuum connection body 166 and vacuum source, respectively. A tubing lumen 169 extends through the vacuum tubing 165 from one end to the opposite end. The tubing lumen 169 is in fluid flow communication with the arm lumen 167 of the vacuum connection body 166 and with the vacuum source and is sized and dimensioned to permit air flow therethrough.

Figure 4:
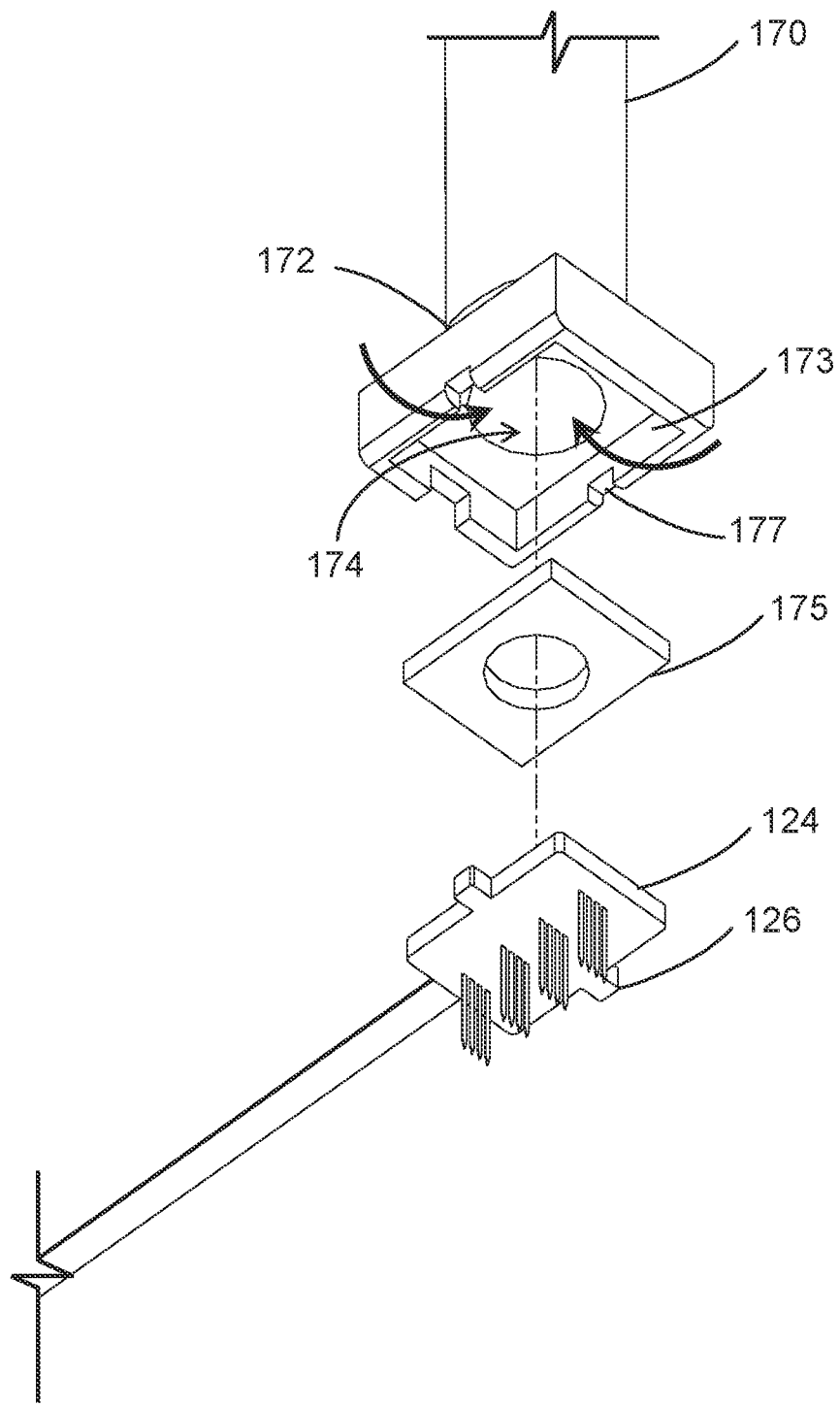
FIG. 4 is an exploded bottom perspective view of the coupler and implant of FIG. 3.
Figure 5:
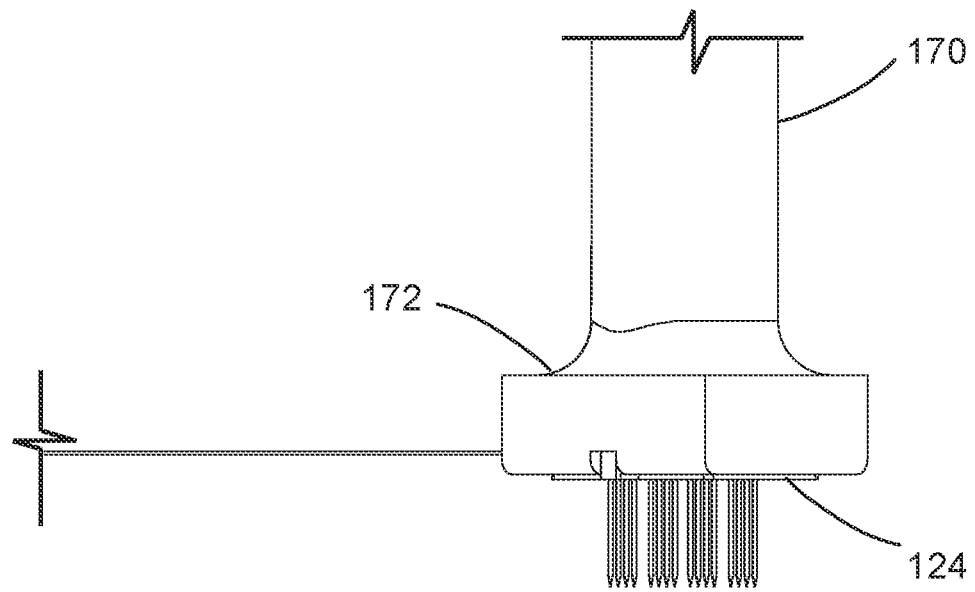
FIG. 5 is a perspective view of the coupler and implant of FIG. 3, shown assembled.
Figure 6:
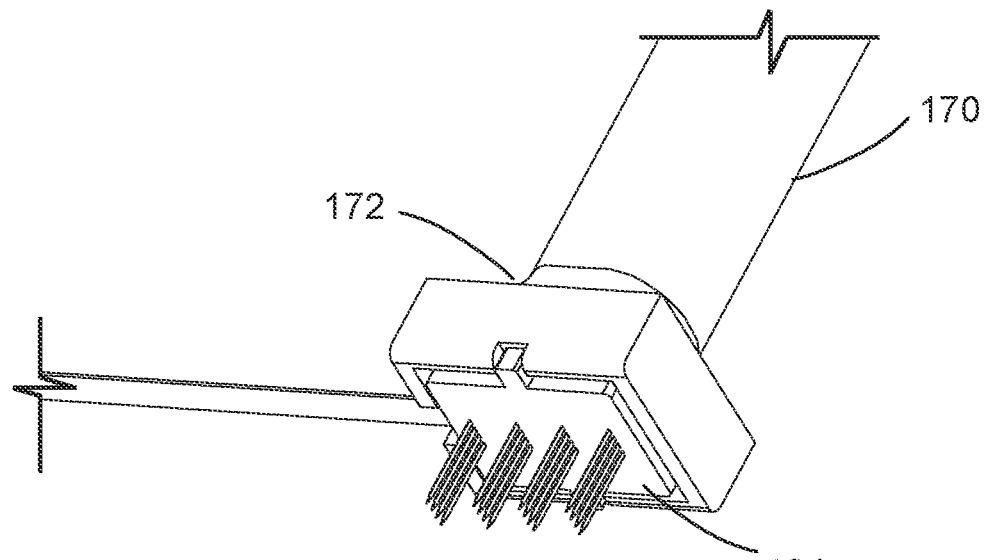
FIG. 6 is a bottom perspective view of the coupler and implant of FIG. 3, shown assembled.
Figure 7A:
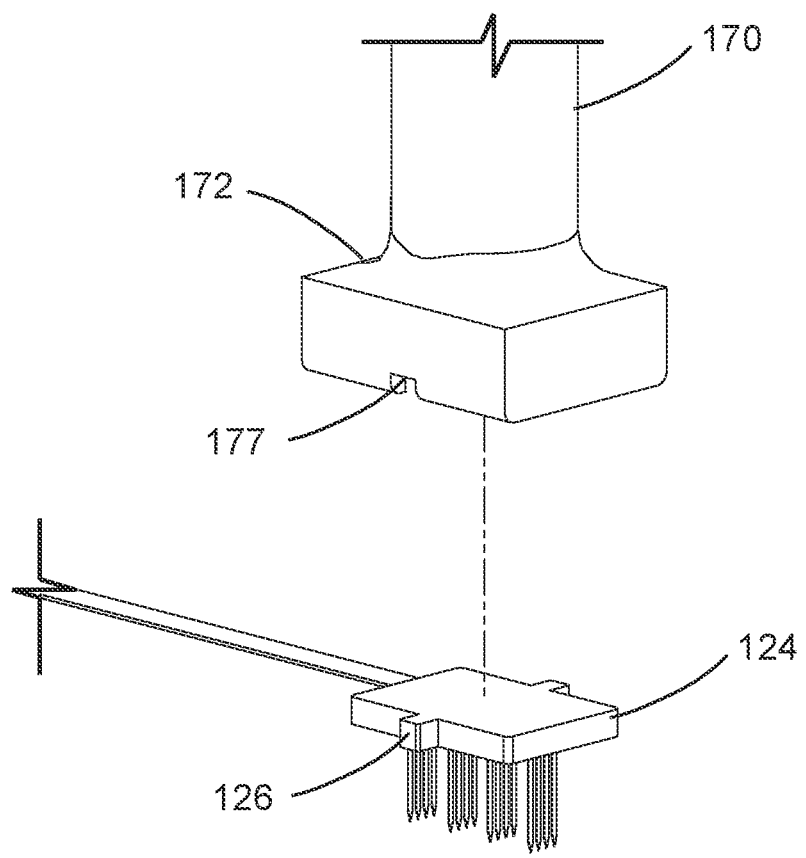
FIG. 7A is an exploded top perspective of a second embodiment of the coupler assembly and implant of the present invention in which a seal is not used.
Figure 7B:
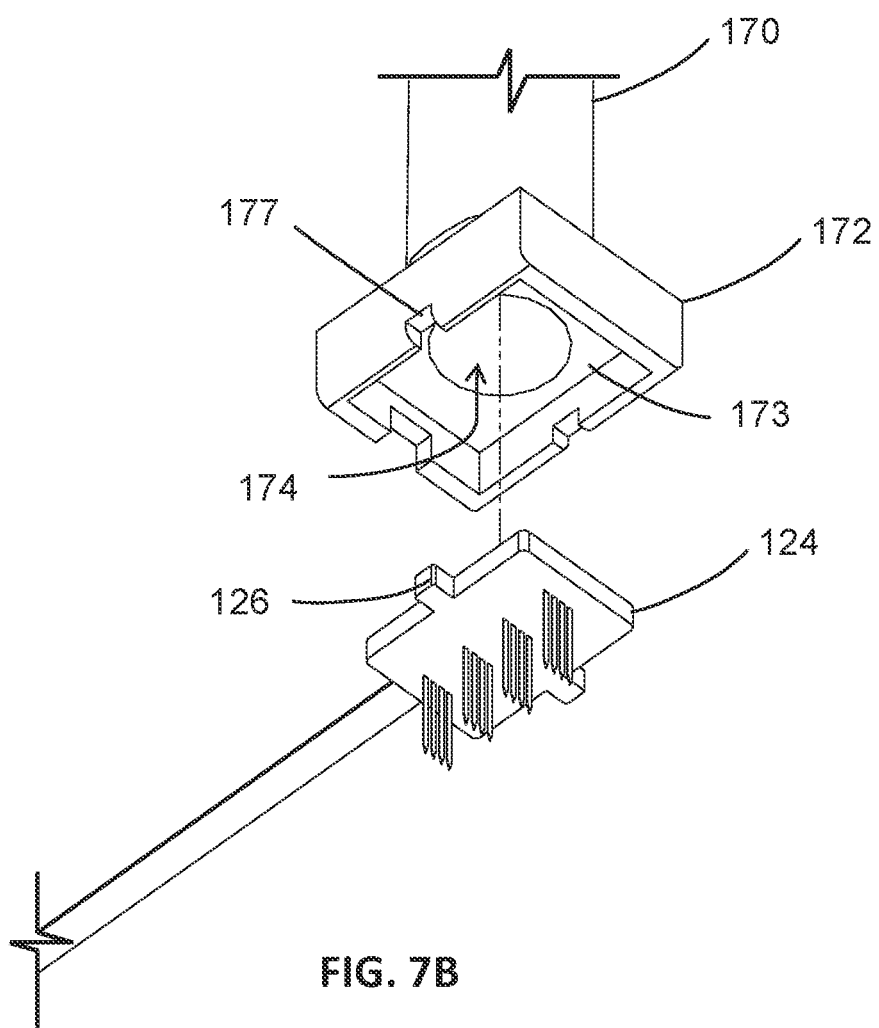
FIG. 7B is an exploded bottom perspective the coupler assembly and implant of FIG. 7A.

The tubing lumen 169, arm lumen 167, body lumen 168 and coupler lumen 174 are in fluid flow communication and collectively define a vacuum path 161. The lumens 169, 167, 168 and 174 may be the same diameter or different diameters as one another. In embodiments where they may be different diameters, adapters may be used to join the vacuum tubing 165, arm 167, vacuum connection body 166 and coupler 170 to modulate between sizes of adjacent components and/or lumens. When the vacuum source is turned on, suction force is produced and is transmitted through the vacuum path 161 created by lumens 169, 167, 168, and 174 to the distal end cavity 173 of the coupler 170 and, in turn, the implant 120. Air is pulled into the coupler lumen 174 through the distal end cavity 173 by the suction force, as shown in FIG. 4, and the base 124 of the implant 120 is held against the wall of the distal end cavity 173 when the implant 120 is brought near enough to the distal end cavity 173 to be affected by the suction force. The coupler 170 may then retain the implant 120, and seal 175 when present, within the distal end cavity 173 for as long as the negative pressure is created by the vacuum source.

In one embodiment, the vacuum source is provided with sufficient negative pressure, or suction force, to pull and hold the implant 120, retaining at least the base 124 of the implant 120 in the distal end cavity 173 when the vacuum source is on. The suction force may be any amount of force suitable to hold the implant 120 based on the size, shape and type of implant 120. For instance, in at least one embodiment the suction force may be between 2 in. Hg and 20 in. Hg, preferably within 5 in. Hg to 10 in. Hg.

Implant Insertion System

Figure 10:
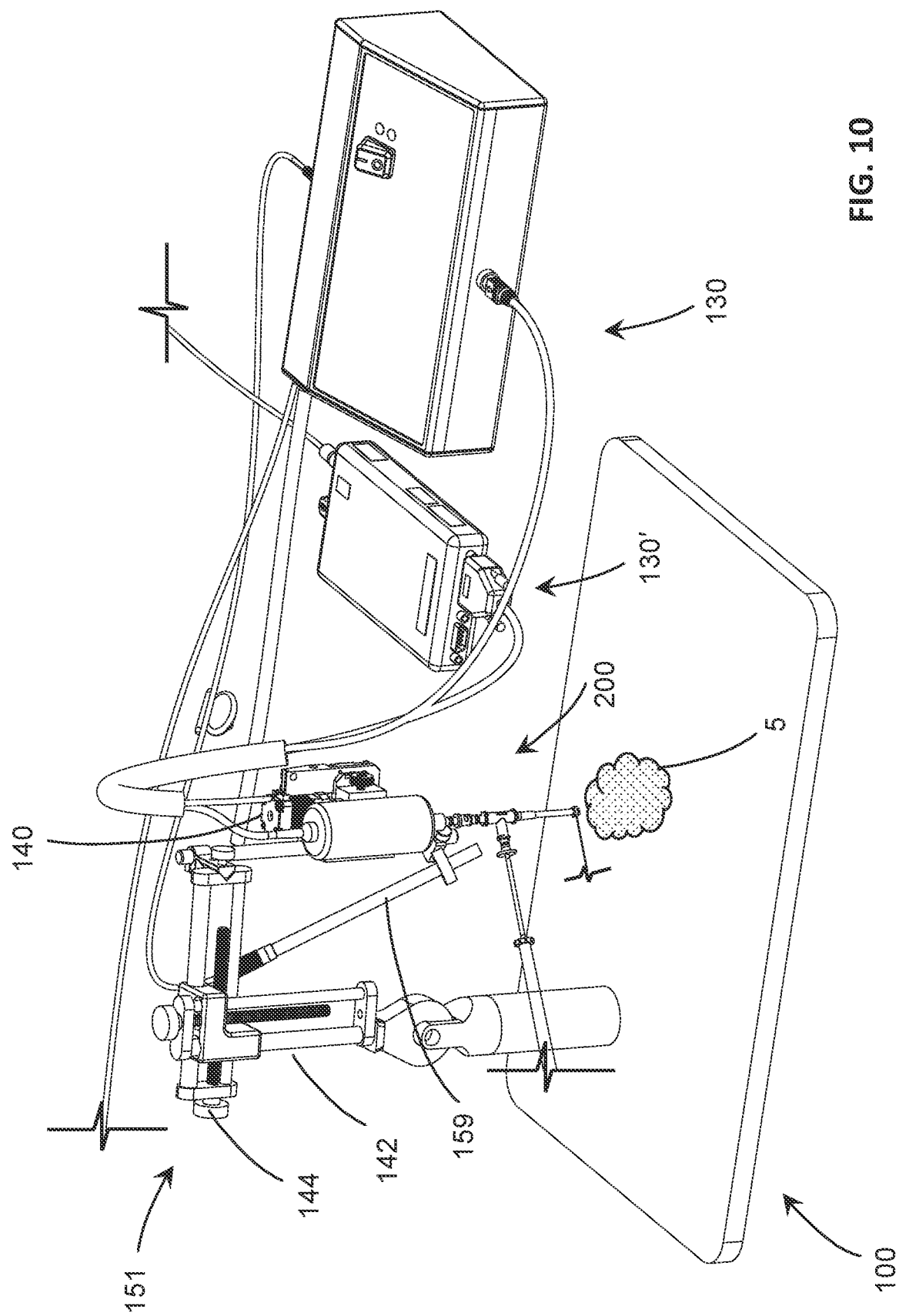
FIG. 10 is a perspective view of one embodiment of the implant insertion system of the present invention, including peripheral hardware.

With reference to FIG. 10, the implant insertion device 200 may be part of a larger implant insertion system 100 that is utilized for advancing and retracting the device 200 for implant placement. The system 100 includes a frame 151 to which the device 200 is mounted or otherwise interconnected. The device 200 may be secured to the frame 151 at any point, though in at least one embodiment it connects through anchor point 112 on the vibrational actuator 110. FIG. 10 shows an exemplary tabletop setting, such as for inserting implants 120 into cortical or brain tissue 5. In other embodiments, the frame 151 may be mounted to and supported on a subject's head, rather than on a table, such as with the placement of deep brain stimulation probes. As shown in FIG. 10, the frame 151 may be stereotaxic or other suitable type and may include a vertical translation bar 142 and horizontal translation bar 144 to provide gross positional adjustments of the device 200 and attached implant 120 relative to the targeted tissue 5. The vertical and horizontal translation bars 142, 144 may be slide bars, screw bolts, rack and pinions, or other suitable adjustment mechanisms. They may be adjusted independently or collectively to position the device 200 and attached implant 120 at any angle in relation to the targeted tissue 5 for insertion, such as but not limited to 15°, 450 and 90° relative to the surface of the tissue 5. This angle defines the angle of an insertion axis 128 along which the implant 120 is inserted. The vertical and horizontal translation bars 142, 144 may also be adjusted, independently or collectively, to position the implant 120 near the target site, which may be a distance in the range of up to 50 mm from the initial starting location, preferably up to 10 mm.

The insertion system 100 may also include a translational motor 140 which connects to the device 200 and is operable to move the device 200 and attached implant 120 along the insertion axis 128 toward the tissue 5 for insertion and retract the device 200 from the insertion site once the implant 120 is successfully embedded. The translational motor 140 may be any suitable motor, such as but not limited to a linear motor, screw driven motor, conveyor belt, track-based motor, rack and pinion motor, rotational motor, hydraulic motor and others. The translational motor 140 may be configured to advance the device 200, and therefore implant 120, along the insertion axis 128 at suitable velocities, such as in the range of about 0.01 mm/s to 1 mm/s in some embodiments, more preferably in the range of about 0.05 mm/s to 0.1 mm/s. In at least one embodiment the translational motor 140 may be operated at a speed of about 0.05 mm/sec where slower speeds lead to less deformation of neural tissue when compared to higher speeds used by other similar systems. The speed of operation of the translational motor 140 may be set or variable and may be determined by the power supplied to it, such as up to 5 watts in at least one embodiment. The translational motor 140 may provide insertion displacements in the range of about 100 µm to 20 cm, and preferably in the range of 100 µm to 10 cm in at least one embodiment.

The implant insertion system 100 also includes at least one control unit 130, as shown in FIG. 10. The control unit 130 may be separate from the rest of the system 100, such as in tabletop embodiments shown in FIG. 10, or may be included within the handpiece for hand-held embodiments.

Regardless of where positioned, and with reference to FIG. 10, the control unit 130 is in electrical communication with the vibrational actuator 110 to provide operative instructions and power for vibration generation. A second control unit 130' may be in electrical communication with the translational motor 140 to provide operative instructions and power for advancing and retracting the device 200, though in some embodiments a single control unit 130 may be in electrical communication with both the vibrational actuator 110 and translational motor 140 and provide operative instructions to each. The control units 130, 130' include a processor that provides instructions for the vibrational actuator 110 and translational motor 140, which may be based on user input to the control unit 130, 130' through an interface (not shown), such as but not limited to LabVIEW-based graphical user interface for control of the vibrational actuator 110 and translational motor 140 with integrated insertion data acquisition. These instructions, which may be provided as electrical impulses such as voltage, are sent from the processor to the vibrational driver and translational driver, respectively. The drivers then relay the instructions for activation and deactivation, as well as the various other operative parameters, to the respective vibrational actuator 110 and translational motor 140. For instance, the vibrational driver may send instructions for vibration amplitude, displacement, frequency, power or other parameters, and may drive the vibrational actuator 110 at or near its resonant frequency, depending on the particular vibrational actuator 110 used and the material and/or tissue being penetrated. The translational driver may provide instructions for speed, position and direction of movement of the translational motor 140. In some embodiments, the control unit(s) 130, 130' may also be in communication with a vacuum source and may send operative instructions to turn the vacuum source on and off, to direct the connection and release of the implant 120 to and from the coupler 170.

In some embodiments, the implant insertion system 100 may also include a visualization aid 159, such as shown in FIG. 10, for viewing and/or visualization of the target insertion site. The lens of the visualization aid 159 may therefore be positioned proximate to the target insertion site to obtain a view of the insertion site. It may also be used to magnify the insertion site for increased accuracy of targeting and placement. In some embodiments, the visualization aid 159 may be a camera, preferably with magnification, as in FIG. 10. In other embodiments, the visualization aid 159 may be a similar magnifier. In other embodiments, it may be or include a laser, such as for targeting, and a light source such as to provide additional lighting for better visualization, particularly when the insertion site is deeper in tissue. In certain embodiments, such as laparoscopic applications, the visualization aid 159 may be inserted through a working channel of the laparoscope to the target site, which may be the same or different working channel through which the implant 120 is inserted.

Though not shown, some embodiments of the insertion device 200 and implant 120 may be compatible in size with minimally invasive surgical approach, such as but not limited to through a 5 mm laparoscopic port or trocar, and where the target neural tissue 5 may be at a distance of about 10 cm and have a diameter of less than 4 mm. The device 200 and implant 120 may therefore be included or housed in a delivery stem having an inner core and surrounding outer sheath. The inner core may be a guide wire or other similar elongate structure that is sufficiently flexible to pass through the curvature necessary for a laparoscopic approach but also rigid enough to provide structural support and transmit vibrations from the vibrational actuator 110 located outside of the laparoscope to the implant 120 at the distal end of the inner core. The outer sheath may be a semi-flexible, low friction material such as Teflon or nylon that surrounds the inner core and enables the delivery stem to be gripped from the outside without significantly damping the oscillation of the inner core. The outer sheath may be retracted for insertion of implant. An endoscopic-style manipulator may also be inserted with flexibility, but then made rigid with a cabling system. A visualization aid 159 may also be inserted through a channel of the laparoscope.

In some applications, such as penetration of peripheral targets like dorsal root ganglion (DRG) and peripheral nerves, insertion is more challenging because the targets are tougher and have increased freedom of movement. In addition, for the peripheral nervous system, anatomy is often more variable between subjects and stereotaxic approaches are far less useful and common. Therefore, surgical approaches for electrode placement may be more reliant on manual, handheld equipment as there is often not a good way to mount hardware or fixturing.

Method of Insertion

Figure 11:
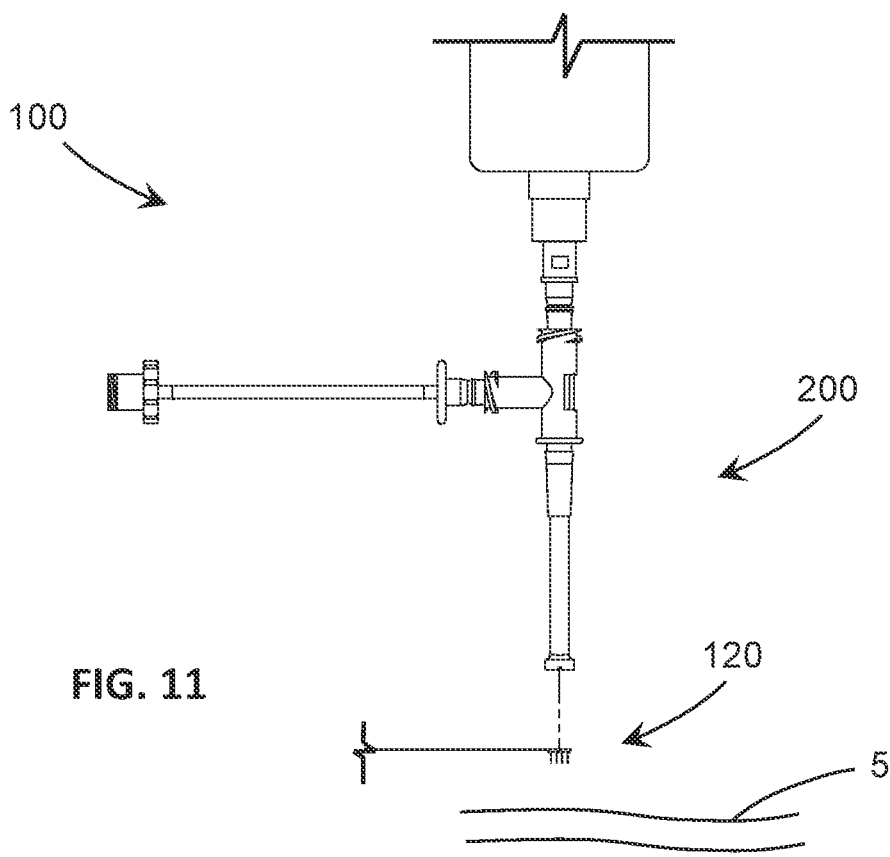
FIG. 11 is a detail view of an illustrative coupler and implant shown prior to loading the implant into the device.

The operation of the implant insertion system 100 when inserting an implant 120 into neural tissue 5 is illustrated in FIGS. 11-14. First, the system 100 begins without an implant 120 loaded in the device 200, as shown in FIG. 11. The device 200 is spaced apart from the neural tissue 5.

Figure 12:
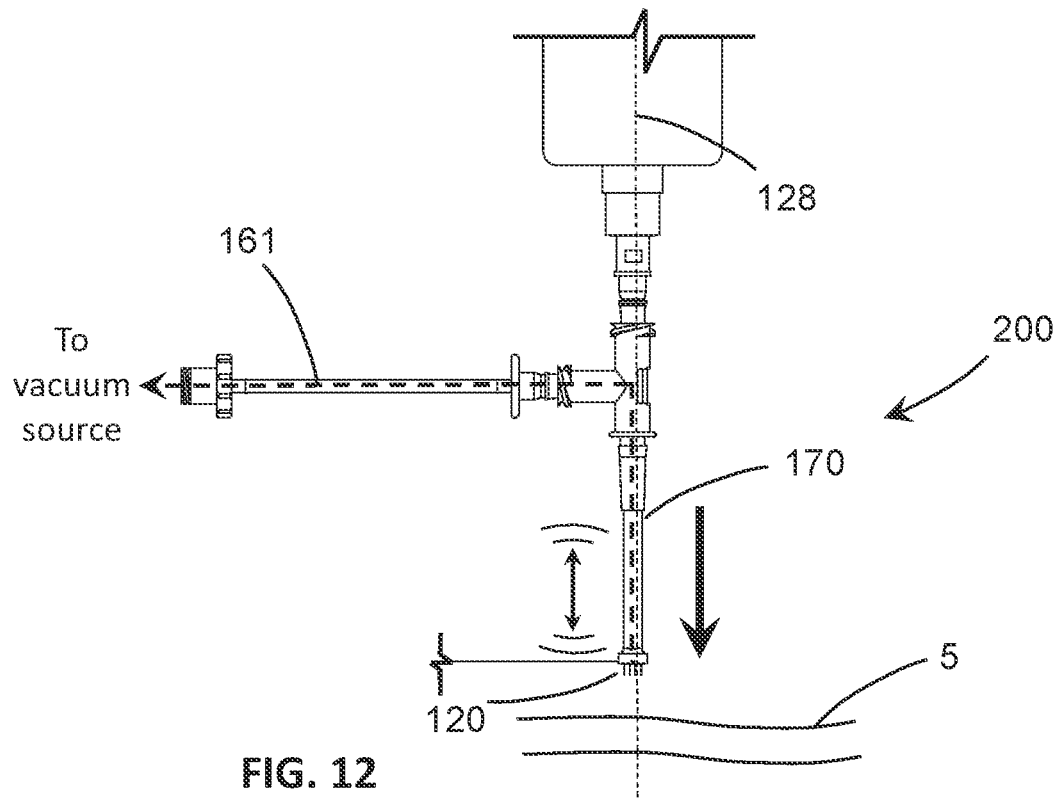
FIG. 12 is a detail view of the coupler and implant of FIG. 11 showing the implant loaded into the device and prior to insertion.

To attach an implant 120, a vacuum source is turned on to create negative pressure in the lumens 169, 167, 168, 174 of the vacuum tubing 165, arm 163, vacuum connection body 166, and coupler 170, respectively. The desired implant 120 is brought in proximity to the distal end cavity 173 of the coupler 170. When the base 124 of the implant 120 is brought sufficiently close to the distal end cavity 173, or is otherwise placed within the distal end cavity 173 of the coupler 170, when the vacuum source is operating and negative pressure flows through the vacuum path 161, the base 124 of the implant 120 is held against the wall of the distal end cavity 173 of the coupler 170 by the vacuum force, retaining the implant 120 in the coupler 170, as shown in FIG. 12. In at least one embodiment, a seal 175 may also be retained in the distal end cavity 173 between the base 124 of the implant 120 and the coupler 170 to facilitate the connection and retention of the implant 120, as explained above.

Figure 13:
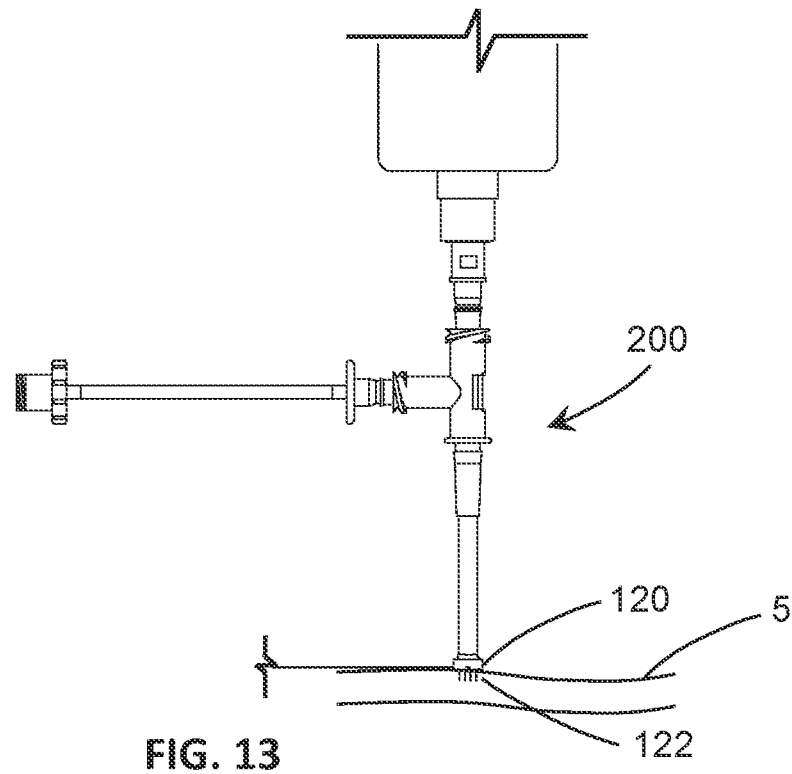
FIG. 13 is a detail view of the coupler and implant of FIG. 12 showing the implant inserted into target tissue.

To insert the implant 120 into target neural tissue 5, the vibrational actuator 110 is turned on, such as by activation of the vibrational driver 134 of the control unit 130, generating oscillations that are transmitted through the coupler 170 and base 124 of the implant 120 to the electrodes 122 of the implant 120. In at least one embodiment, the oscillations are generated and propagated axially in the direction of the insertion axis 128, shown in FIG. 12. The translational driver of the control unit 130 is then activated to advance the neural implant insertion device 200 toward the target neural tissue 5, causing the electrode(s) 122 of the implant 120 to pierce the tissue 5 upon contact and penetrate into the tissue 5 until the desired location within the tissue 5 is reached, as shown in FIG. 13. Achieving the desired location within the tissue 5 may be determined in various ways, such as but not limited to visually, with enhancements to vision such as microscopy, or when the frame 151 carrying the device 200 is advanced a predetermined distance according to calculations based on the position of the frame 151, device 200, tissue 5 and desired placement within the tissue 5. The oscillations transmitted through the device 200 to the electrode(s) 122 during insertion reduce the force the electrode(s) 122 apply to the tissue 5 upon piercing and therefore also reduce dimpling, ancillary damage, and provide a more precise delivery of the tip of the electrode(s) 122 to the desired location within the tissue 5. In some embodiments, a visualization aid 159, as described above in greater detail, may be used to confirm placement of the implant 120 relative to the neural tissue 5. Additional adjustments to the insertion depth of the implant 120 may be made as necessary until the desired placement is achieved and confirmed. Once the desired positioning of the implant 120 is confirmed, the vibrational actuator 110 is turned off, the oscillations no longer being necessary.

Figure 14:
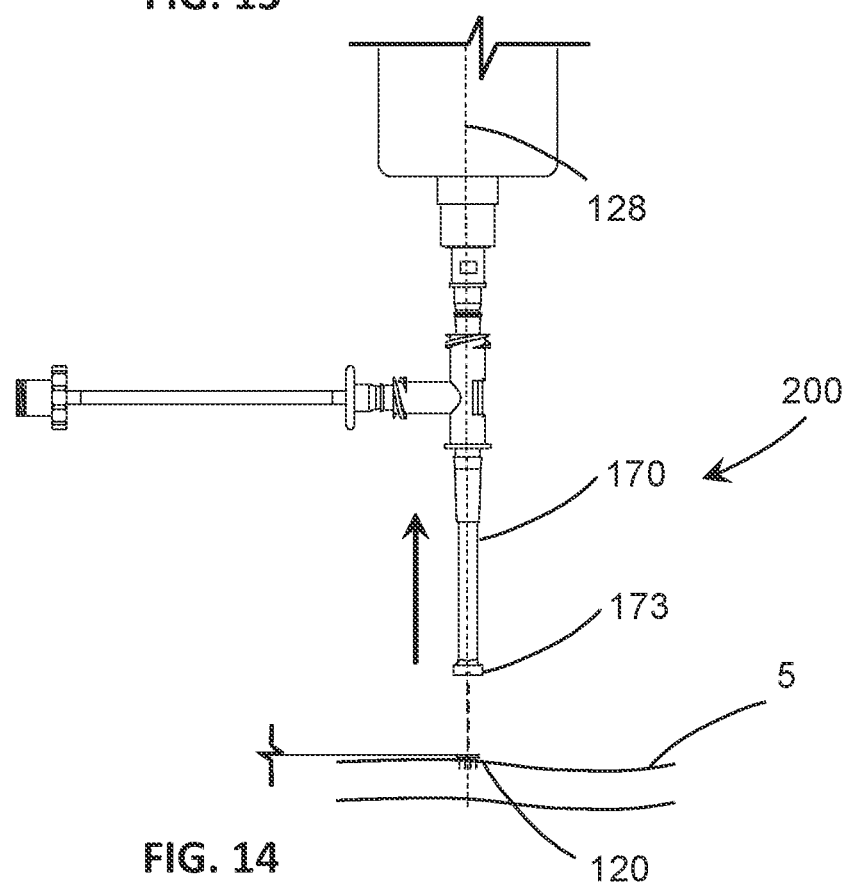
FIG. 14 is a detail view of the coupler and implant of FIG. 13 showing the implant detached from the device and the remainder of the device retracted from the tissue post-insertion.

To remove the insertion device 200, as shown in FIG. 14, the vacuum source is turned off. This causes the negative pressure exerted on the implant 120 to cease. The force holding the base 124 of the implant 120 to the distal end cavity 173 of the coupler 170 is no longer present and the base 124 is therefore released from the distal end cavity 173. Since the vacuum source is located remotely from the tissue 5, turning off the vacuum source does not alter the placement or positioning of the implant 120 within the tissue 5. Once the vacuum source is turned off and the implant 120 decoupled from the coupler 170, the translational driver 136 may again be engaged to move the device 200 along the insertion axis 128, but in the reverse direction, to remove the device 200. This allows the coupler 170 to be pulled back from the implant 120 without disturbing the final insertion position of the implant 120.

Though described in terms of moving the device 200 toward and away from stationary tissue 5 for delivery of the implant 120, the reverse is also contemplated. In such embodiment, the tissue may be loaded on a stage which may be mobile relative to a stationary device 200. Motors may be used to move the stage to advance the tissue 5 toward the device 200 until electrode penetration and insertion is achieved, then retract the tissue 5 with embedded implant once the vacuum is turned off and the implant 120 is released from the device 200.

Since many modifications, variations and changes in detail can be made to the described preferred embodiments, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A device for inserting an implant into target tissue, said device comprising:
    a vibrational actuator configured to generate vibrations when activated;
    a coupler having:
    (i) a proximal end mechanically interconnected with said vibrational actuator;
    (ii) a distal end opposite said proximal end, said distal end configured to selectively retain said implant; and
    (iii) a coupler lumen extending between said proximal and distal ends;
    a vacuum assembly mechanically interconnecting said vibrational actuator and said coupler and transmitting said vibrations from said vibrational actuator to said coupler, said vacuum assembly including a vacuum connection body having a body lumen extending through at least a portion of said vacuum connection body, said vacuum connection body connected to said coupler with said body lumen in fluid flow communication with said coupler lumen, said body lumen further interconnectable in fluid flow communication with a vacuum source, wherein said body lumen and said coupler lumen collectively at least partially define a vacuum path between the vacuum source and said distal end of said coupler;
    said vacuum path dimensioned to permit air flow in a negative pressure from said distal end of said coupler through said coupler lumen and said body lumen to the vacuum source upon activation to selectively retain said implant to said distal end of said coupler and to selectively release said implant from said distal end of said couple by deactivation of the vacuum source; and
    said coupler simultaneously transmitting said vibrations to said implant and facilitating said air flow in a negative pressure at said implant sufficient to retain said implant at said distal end of said coupler.

2. The device of claim 1, wherein said distal end of said coupler further comprises a distal end cavity defined between cavity walls, said distal end cavity being correspondingly dimensioned to at least a portion of said implant and configured to receive said portion of said implant.

3. The device of claim 2, wherein said implant includes a base and at least one electrode extending from said base and said distal end cavity is correspondingly shaped and configured to receive said base of said implant.

4. The device of claim 2, wherein said base includes at least one tab extending outwardly therefrom, at least one of said cavity walls of said distal end defining at least one notch correspondingly dimensioned to receive said at least one tab.

5. The device of claim 4, wherein said implant receives said vibrations from contact between said tab within said notch and said distal end.

6. The device of claim 2, wherein said implant includes a base, at least one electrode extending from said base, and a cable in electrical communication with said at least one electrode, at least one of said cavity walls defining a recess dimensioned to receive said cable.

7. The device of claim 1, further comprising a seal located at said distal end of said coupler, said seal defining an aperture correspondingly dimensioned and aligned in fluid flow communication with said coupler lumen.

8. The device of claim 7, wherein said implant includes a base, at least one electrode extending from said base, said seal is interposed between said distal end of said coupler and said base of said implant, said seal being compressible to conform to each of said distal end and said base of said implant.

9. The device of claim 1, wherein said vibrational actuator is capable of generating axial vibrations along an insertion axis; said implant includes a base and at least one electrode extending from said base; and said vibrational actuator, said coupler, and said implant are aligned along said insertion axis, said insertion axis coincident with a length of said at least one electrode of said implant.

10. The device of claim 1, wherein said vibrational actuator is configured to generate vibrations in the ultrasonic range of 0.1-20 μm.

11. The device of claim 1, wherein said vibrational actuator is configured to operate at a resonant frequency in the range of 20-100 kHz.

12. The device of claim 11, wherein said vibrational actuator is configured to operate at a resonant frequency in the range of 20-40 kHz.

13. The device of claim 1, wherein said vacuum connection body further comprising an arm extending therefrom, said arm including an arm lumen extending therethrough in fluid flow communication with said body lumen and said tubing lumen, said arm lumen forming part of said vacuum path.

14. The device of claim 1, wherein said vacuum assembly further comprises a vacuum tubing having a tubing lumen extending through said vacuum tubing, said vacuum tubing connectable to the vacuum source at one end and connected to said vacuum connection body at an opposite end, said tubing lumen in fluid flow communication with the vacuum source and said body lumen; and said tubing lumen, said body lumen and said coupler lumen collectively defining said vacuum path.

15. The device of claim 1, wherein said vacuum path is dimensioned to permit negative pressure in the range of 2 in Hg-20 in Hg.

16. The device of claim 1, wherein said vacuum path is dimensioned to permit negative pressure in the range of 5 in Hg-10 in Hg.

17. An implant insertion system, comprising:
a frame;
the device as recited in claim 1 mounted to said frame;
a translational motor connected to said device and configured to move said device along an insertion axis when activated; and
a control unit in electrical communication with said vibrational actuator of said device and configured to provide operative instructions to said vibrational actuator to generate vibrations, said control unit further in electrical communication with said translational motor and configured to provide operative instructions to said translational motor to activate said translational motor and direct movement of said device along said insertion axis.

18. The implant insertion system of claim 17, wherein said translational motor is configured to move said device along said insertion axis at displacements in the range of 100 µm to 20 cm.

19. The implant insertion system of claim 17, wherein said translational motor is configured to move said device along said insertion axis at speeds in the range of 0.01 mm/s-1 mm/s.

20. A method of inserting an implant into tissue comprising:
aligning a device comprising a vibrational actuator, a vacuum connection body, and a coupler with target tissue;
bringing an implant having a base and at least one electrode extending from said base within proximity to a distal end of said coupler;
activating a vacuum source interconnected to said vacuum connection body and creating air flow in a negative pressure between said implant and said distal end of said coupler, said negative pressure transferring from said vacuum source, through said vacuum connection body and said coupler, to said distal end of said coupler, and selectively retaining said implant against said distal end of said coupler as a result of said negative pressure;
oscillating said at least one electrode by activating said vibrational actuator and transmitting vibrations from said vibrational actuator, through said vacuum connection body and said coupler, and to said implant at said distal end of said coupler;
advancing said device with said implant along an insertion axis toward said target tissue until said at least one electrode penetrates said tissue to a desired depth;
deactivating said vibrational actuator; and
selectively releasing said implant from said coupler by deactivating said vacuum source.

21. The method of claim 20, wherein said vibrations are generated and propagated through said device axially along said insertion axis.

22. The method of claim 20, wherein advancing said device with said implant occurs at speeds in the range of 0.01 mm/s-1 mm/s.

* * * * *